United States Patent [19]
Shalaby et al.

[11] Patent Number: 4,605,730
[45] Date of Patent: Aug. 12, 1986

[54] SURGICAL ARTICLES OF COPOLYMERS OF GLYCOLIDE AND ε-CAPROLACTONE AND METHODS OF PRODUCING THE SAME

[75] Inventors: Shalaby W. Shalaby, Lebanon; Dennis D. Jamiolkowski, Long Valley, both of N.J.

[73] Assignee: Ethicon, Inc., Somerville, N.J.

[21] Appl. No.: 743,117

[22] Filed: Jun. 10, 1985

Related U.S. Application Data

[62] Division of Ser. No. 432,176, Oct. 1, 1982, abandoned.

[51] Int. Cl.⁴ .............................................. C08G 63/10
[52] U.S. Cl. .................................... 528/357; 525/415; 528/354; 528/358; 128/335.5
[58] Field of Search ...................... 528/354, 357, 358; 525/415

[56] References Cited

U.S. PATENT DOCUMENTS

| | | | |
|---|---|---|---|
| 2,890,208 | 6/1959 | Young et al. | 528/357 |
| 3,284,417 | 11/1966 | Hostettler et al. | 528/357 |
| 3,784,585 | 1/1974 | Schmitt et al. | 528/354 X |
| 4,045,418 | 8/1977 | Sinclair | 528/357 |
| 4,057,537 | 11/1977 | Sinclair | 528/357 X |
| 4,157,437 | 6/1979 | Okuzumi et al. | 525/415 X |

Primary Examiner—Earl Nielsen
Attorney, Agent, or Firm—Robert L. Minier

[57] ABSTRACT

Novel copolymers of ε-caprolactone and glycolide useful in making surgical articles and particularly surgical sutures having Young's modulus of less than 250,000 psi. New and improved polymerization methods for producing the novel ε-caprolactone and glycolide copolymers.

6 Claims, No Drawings

SURGICAL ARTICLES OF COPOLYMERS OF GLYCOLIDE AND ε-CAPROLACTONE AND METHODS OF PRODUCING THE SAME

This is a division of application Ser. No. 432,176, filed Oct. 1, 1982, and now abandoned.

BACKGROUND OF THE INVENTION

1. Field of Invention

This invention relates to synthetic surgical devices having improved properties made from copolymers of glycolide and ε-caprolactone and, more particularly, to oriented filaments and sutures prepared from such polymers and to methods of manufacturing such polymers.

2. Description of the Prior Art

Homopolymers and copolymers of lactide and glycolide are well known in the preparation of synthetic absorbable sutures as disclosed, for example, in U.S. Pat. Nos. 3,636,956; 2,703,316; 3,468,853; 3,865,869, and 4,137,921. Also, in U.S. Pat. No. 3,867,190, it is known to include certain cylic comonomers with glycolide including ε-caprolactone. In fact, the use of cylic ester monomers in the formation of polyesters for the fabrication of synthetic surgical articles is well known in the art. The conventional polymerization method of forming polymers of the cylic esters is through ring opening polymerization. In U.S. Pat. No. 4,300,565, there is disclosed surgical articles fabricated from synthetic absorbable copolymers formed by copolymerizing glycolide with a cylic ester monomer in a specific manner. Hence, it should be appreciated that broadly copolymers of ε-caprolactone and other cyclic esters, such as lactide or glycolide, are well known and described in the art as well as are various methods for their production.

The synthetic absorbable sutures have gained considerable acceptance in the surgical field; however, the "handleability" or the compliance; i.e., flexibility and "limpness", has not always been considered satisfactory in monofilament configurations. It is believed that monofilament constructions are more suitable for surgical uses than the multifilament or braided configurations as they tend to produce less infection and trauma at the wound closure site. However, the monofilaments tend to be stiffer and harder to handle than the braided configuration of the same diameter. Over the years, various polymer combinations have been tried in an attempt to obtain the desired very delicate interplay between the properties of suture absorbability, in vivo strength retention, initial knot strength, and high compliance or low modulus. These desired properties, other than absorbability, are obtained in some suture materials; for example, in those described in commonly assigned copending patent applications Ser. No. 311,829 filed Oct. 16, 1981, and Ser. No. 338,407 filed Jan. 8, 1982. The suture materials described have the desired strengths, compliance and flexibility but are not absorbable and, hence, are limited in their use. To the best of our knowledge the only synthetic, absorbable sutures which in some instances may have the properties as described above are those made from polydioxanone as described in U.S. Pat. No. 4,052,988.

It should be appreciated, that to design molecular chains needed for the production of highly compliant absorbable materials, an obvious route is to copolymerize suitable comonomers or mixtures of pre-polymers and monomers following procedures similar to those used in the formation of compliant non-absorbable sutures. However, such is not the case for those polymers are of the AA-BB non-absorbable type. Furthermore, copolymerizing comonomers of glycolide and ε-caprolactone following the teaching of U.S. Pat. No. 3,867,190 which describes the copolymers containing 15% or less of the ε-caprolactone moieties does not produce compliant materials. Copolymers containing less than 15% caprolactone are random in nature and the monofilaments made therefrom display high modulus and low compliance. It is known that copolymers containing less than 85% glycolide moieties with random microstructure do not generally offer good fiber forming polymers because of their improper level of crystallinity. Hence it would be expected that copolymers containing more than 15% caprolactone sequences would have poor crystallinity and be virtually amorphous and unsuitable for the production of strong monofilament suture materials.

SUMMARY OF THE INVENTION

The present invention describes new copolymers containing specific weight percents of epsilon (ε)-caprolactone and specific weight percents of glycolide or a mixture of glycolide and lactide. These new copolymers produce synthetic absorbable surgical articles having new and novel properties and produce filaments or suture materials having desirable straight and knot tensile strengths, controllable absorbability, suitable in vivo strengths while unexpectedly displaying unique high compliance characteristics and low modulus. In accordance with the present invention, the new copolymers have a tensile strength of at least 30,000 psi and a Young's modulus of less than 350,000 psi. When in filament form, sutures made from our novel copolymers preferably have a tensile strength of at least 50,000 psi and a Young's modulus of less than 250,000 psi. The novel copolymers of the present invention comprise from about 20 to 35 weight percent of ε-caprolactone and from 65 to 80 weight percent of glycolide or mixtures of glycolide and lactide. In preferred embodiments of the present invention, when mixtures of glycolide and lactide are used, the mixture should contain less than 20 percent by weight of L(−)lactide. The new copolymers may be used as molded or shaped articles or they may be fabricated into filaments and appropriate sutures by techniques well known in the art and may have needles attached to said suture as desired. The filaments may be annealed to produce materials having tensile strengths of at least 50,000 psi while maintaining a Young's modulus of less than 250,000 psi. Our new copolymers may be designed to retain in vivo strengths of at least 40 percent after 7 days while being completely absorbed in vivo in less than 150 days. In certain embodiments of the present invention the novel copolymers have inherent viscosities of at least 0.8 dl/g as determined on a 0.1 g/dl solution in hexafluoroisopropanol (HFIP) at 25° C. In certain embodiments of the present invention, our novel copolymers have a crystallinity of at least 5% and preferably at least 10%.

Also in accordance with the present invention, our novel copolymers are produced by polymerizing a mixture of glycolide and ε-caprolactone in the presence of from about 0.004 to 0.02 weight percent of catalyst. The catalyst may be a metal salt or oxide, preferably a tin salt or oxide as, for example, stannous octoate, dibutyltin oxide and the like. The polymerization is carried out at a temperature of below 250° C. for a period of time sufficient to produce a conversion of the monomers to polymer of at least 80%. In other novel processes for producing the copolymers of the present invention, a first step is used to produce a low molecular weight copolymer of ε-caprolactone and glycolide. In the first step, the copolymer should comprise at least 50% by weight of ε-caprolactone to obtain an ε-caprolactone rich pre-polymer. The first step is carried out at a temperature of below 220° C. and is followed by a second step wherein additional glycolide is added to the pre-polymer. This additional mixture is polymerized at a temperature of above 120° C. for a period of time sufficient to produce a conversion of at least 80%.

Polymers produced by the methods described above may be readily extruded and drawn as is well known in the art to produce oriented filamentary material. The oriented filaments may be used with or without annealing to produce sutures. Needles may be attached to the oriented filaments to produce needled sutures. The sutures with or without needles may be sterilized by well known sterilization techniques to produce new and novel sterile surgical sutures. The polymers may also be fabricated by other techniques such as injection molding and the like and then sterilized by techniques well known in the art to produce new and novel sterile synthetic devices.

DETAILED DESCRIPTION OF THE PRESENT INVENTION

In the following description and examples, all parts and percentages are by weight unless otherwise specified.

The method of the present invention comprises either a single stage or a two-stage polymerization process. In the single stage polymerization process, an essentially random copolymer of glycolide monomer with ε-caprolactone is produced. The polymerization is carried out in a conventional manner using a polymerization reactor equipped with heating and stirring means. The polymerization is carried out in the presence of from about 0.004 to 0.02 weight percent of a metal salt or metal oxide, preferably dibutyltin oxide or stannous octoate. The polymerization is conducted with pure and dry reactants and under a dry and inert atmosphere at temperatures sufficient to maintain the reaction mixture at a temperature close to the melting point of the polymer being produced. The amount of ε-caprolactone should be sufficient so that in the final copolymer there will be from about 20 percent by weight to 35 percent by weight of the ε-caprolactone moieties. The amount of glycolide used should be sufficient so that in the final polymer there is from about 65 weight percent to about 80 weight percent of the glycolide moieties. The polymerization should be conducted for a time sufficient to have a conversion of the monomers to copolymer of at least 80 percent and preferably more than 90 percent.

The following example describes a preferred copolymer of the present invention as well as a preferred method for producing the copolymer.

EXAMPLE I

A flame dried 100 ml glass ampoule equipped with a Teflon-coated magnetic spinbar is charged with 14.27 grams (0.125 mole) of ε-caprolactone, 43.53 grams (0.375 moles) glycolide 0.0591 grams 1,6-hexanediol and a catalytic amount of stannous octoate (0.25 ml of a 0.033 molar solution in toluene). The pressure in the ampoule is reduced to evaporate the toluene. The ampoule is repeatedly purged and vented with dry nitrogen and the pressure adjusted with dry nitrogen to about ¾ of an atmosphere. The ampoule is sealed with a flame. The sealed ampoule is immersed in a silicone oil bath preheated to 100° C. This temperature is maintained for 15 minutes, with stirring as long as possible, and the temperature increased to 150° C. which is maintained for 15 minutes. The temperature is raised to 190° C. and the polymerization continued for 18 hours at 190° C. The resultant copolymer is isolated, chilled, ground, and dried under vacuum at room temperature. Some unreacted monomer is removed by heating the ground copolymer under vacuum at 110° C. for 16 hours. Approximately 95 percent conversion of monomers to copolymer is obtained. The resultant copolymer comprises 23 percent by weight of ε-caprolactone moieties and 77 percent by weight glycolide moieties. The inherent viscosity of the resultant copolymer is 1.66 dl/g as measured using a 0.1 g/dl solution in hexaflourisopropanol (HFIP) at 25° C.

EXAMPLE II

For comparison purposes, Example 6 described in U.S. Pat. No. 3,867,190 which describes a glycolide copolymer with 15 weight pecent ε-caprolactone is carried out.

A flame dried 100 ml glass ampoule equipped with a Teflon-coated magnetic spinbar is charged under dry and oxygen free conditions with 6.0 grams (0.053 mole) ε-caprolactone, 34.0 grams (0.293 mole) glycolide and 0.12 glram litharge. After repeated purging with nitrogen the pressure is adjusted with nitrogen to about ¾ of an atmosphere and the ampoule is flame sealed. The sealed ampoule is immersed in a silicone oil bath and heated to 145° to 150° C. The ampoule is maintained in this temperature range for 31 hours. The copolymer is isolated, ground and dried under vacuum at room temperature. Some unreacted monomer is removed by heating the ground copolymer at reduced pressure at 110° C. for 16 hours. The conversion of monomers to copolymer is approximately 97 percent. The resultant copolymer comprises 15 percent by weight of ε-caprolactone moieties and 85 percent by weight of glycolide moieties. The resultant copolymer is practically insoluble in HFIP.

Attempts to extrude and draw the copolymer to produce an oriented filament are unsuccessful as the copolymer undergoes degradation at the temperature required to obtain a uniform melt.

EXAMPLE III

An attempt to make a suitable filament forming copolymer in accordance with the teachings of U.S. Pat. No. 3,867,190 using the amounts and types of catalyst in accordance with the methods of the present invention is conducted.

A flame dried 100 ml glass ampoule equipped with a Teflon-coated magnetic spinbar is charged under dry and oxygen-free conditions with 6.0 grams (0.053 mole) ε-caprolactone, 34.0 grams (0.293 mole) glycolide, and 0.90 ml of a 0.33 molar stannous octoate in toluene solution. The pressure in the ampoule is reduced to remove the toluene. After repeated purging and venting with nitrogen the pressure is adjusted with nitrogen to about ¾ of an atmosphere and the ampoule flame sealed. The sealed ampoule is immersed in a silicone oil bath and heated to 145° to 150° C. This temperature range is maintained for 31 hours. The copolymer is isolated, ground and dried under vacuum at room temperature. Some unreacted monomers are removed by heating the ground copolymer at reduced pressure at 110° C. for 16 hours. Approximately 97% conversion of monomers to copolymer is obtained. The resultant copolymer comprises 15 percent by weight of ε-caprolactone moieties and 85 percent by weight of glycolide moieties. The resultant copolymer is practically insoluble in HFIP. The resultant copolymer is not extrudable and orientable so as to produce filament satisfactory for producing sutures. On trying to extrude the resultant copolymer it undergoes degradation at the temperature range necessary to maintain a uniform melt.

In preferred embodiments of the single step method for producing the copolymers of the present invention, it is desired that about 22 percent to 32 percent by weight of the ε-caprolactone moiety be obtained in the final polymer.

As previously described, an alternate novel method for producing the new copolymers of the present invention is to initially form a low molecular weight pre-polymer of ε-caprolactone and glycolide. This pre-polymer is rich in ε-caprolactone; that is, it comprises at least 50 weight percent of ε-caprolactone. The prepolymer is produced at temperatures below about 220° C. Once the pre-polymer is formed, additional glycolide or glycolide/caprolactone or lactide mixture rich in glycolide is added to the pre-polymer and the resultant mixture further polymerized at temperatures of from about 120° C. to 250° C. and preferably from about 180° C. to 240° C. This two step polymerization is carried out to a conversion of at least 85 percent.

The following is a specific example of this alternate method for producing the novel copolymers of the present invention.

EXAMPLE IV

A flame dried multineck glass reactor is charged under dry and oxygen free conditions with 71.8 grams (0.629 mole) ε-caprolactone, 31.3 grams (0.27 mole) glycolide, 0.0882 gram glycolic acid and 0.43 ml. of a 0.33 molar stannous octoate in toluene solution. The reactor is outfitted with an adapter with a hose connection and a dry mechanical stirrer. The pressure in the reactor is reduced and the toluene removed. The reactor is purged and vented with nitrogen which is maintained at a pressure of one atmosphere for the remainder of the run. The reactor is immersed in a silicone oil bath and heated to 120° C. which is maintained for 10 minutes. Over the course of 30 minutes the temperature is increased to 200° C. which is maintained for 20 minutes. The bath is allowed to cool to 150° C., the stirrer is stopped and the reactor withdrawn from the bath. A small sample, about 0.2 grams, of the reaction mass is withdrawn under a blanket of nitrogen. The sample has an inherent viscosity of 0.51 dl/g. To the reactor is added 45.6 grams (0.399 mole) ε-caprolactone and 185.6 grams (1.599 moles) glycolide. The reactor is reintroduced into the silicone oil bath. The temperature drops to 120° C. which is maintained for 10 minutes while providing good stirring. In the course of 15 minutes the temperature is increased to 205° C. which is maintained for 4 hours.

The copolymer is isolated, ground, and dried under vacuum at room temperature. Some unreacted monomers are removed by heating the ground copolymer at reduced pressure at 100° C. to constant weight. A conversion of monomers to copolymer of approximately 87% is obtained. The resultant copolymer comprises 26 percent by weight of ε-caprolactone moieties and 74 percent by weight of glycolide moieties. The resultant copolymer has an inherent viscosity of 1.53 dl/g as measured using a 0.1 g/dl solution in HFIP at 25° C.

EXAMPLE V

The procedure of Example I is essentially followed as set out in that example except that the ampoule is charged with 17.1 grams (0.150 mole) ε-caprolactone, 40.6 grams (0.350 mole) glycolide, 0.1182 gram (0.001 mole), 1,6-hexanediol, and 0.25 ml. of a 0.033 molar stannous octoate in toluene solution. The sealed ampoule is immersed in a silicone oil bath preheated to 100° C. This temperature is maintained for 30 minutes with stirring as long as possible. In the course of 50 minutes the temperature is raised to 190° C. which is maintained for 7 hours. The percent conversion of monomers to copolymer is approximately 90% and the resultant copolymer has an inherent viscosity of 1.24 dl/g as measured using a 0.1 g/dl solution in HFIP at 25° C. The resultant copolymer comprises 23 percent by weight of ε-caprolactone moieties.

EXAMPLE VI

The procedure of Example I is followed as set out in that example except that the ampoule is charged with 14.3 grams (0.125 moles) ε-caprolactone, 43.5 grams (0.35 mole) glycolide, 0.0591 gram (0.0005 mole) 1,6-hexanediol, and 0.51 ml. of an 0.033 molar stannous octoate in toluene. The sealed ampoule is immersed in a silicone oil bath preheated to 100° C. That temperature is maintained for 15 minutes and then increased over the course of less than an hour to 195° C. which is maintained for 2 hours. The copolymer is isolated, ground and dried under vacuum at room temperature. Some unreacted monomer is removed by heating the ground copolymer at reduced pressure at 110° C. for 16 hours. The conversion of monomers to copolymer is approximately 90%. The resultant copolymer has an inherent viscosity of 1.62 dl/g measured at 25° C. at a 0.1 g/dl concentration in HFIP. The resultant copolymer comprises 17 percent by weight of ε-caprolactone moieties.

EXAMPLE VII

The procedure as set forth in Example IV is followed as set forth therein except the reactor is charged with 22.8 grams (0.200 mole) ε-caprolactone, 10 grams (0.0862 mole) glycolide, 33.8 mg (0.286 mmole) 1,6-hexanediol, and 0.216 ml. of a 0.33 molar stannous octoate in toluene solution. The charged reactor is immersed in a silicone oil bath and heated to 190° C. over the course of 35 minutes. Heating is discontinued and the reactor in the bath allowed to cool to 120° C. over a period of 30 minutes. While maintaining the temperature at 120° C. and under a nitrogen blanket 6.5 grams (0.057 mole) ε-caprolactone and 59.7 grams (0.514 mole) glycolide is added to the reactor. The reaction mass is maintained at 120° C. for 40 minutes with good stirring. Over the course of 15 minutes the temperature is increased to 195° C. which is maintained for 2½ hours. The copolymer is isolated, ground and dried under vacuum at room temperature. Some unreacted monomers are removed by heating the ground copolymer at reduced pressure at 85° C. for 16 hours. A conversion of monomer to polymer of greater than 90% is obtained. The resultant copolymer has an inherent viscosity of 1.60 dl/g as measured during a 0.1 g/dl concentration in HFIP at 25° C.

The resultant copolymer comprises 26 percent by weight of ε-caprolactone moieties.

EXAMPLE VIII

The procedure as set forth in Example VII is carried out as set forth therein with the exception that the reactor is charged with 22.8 grams (0.200 mole) ε-caprolactone, 7.7 grams (0.066 mole) glycolide, 0.1182 gram (0.001 mole) 1,6-hexanediol and 0.25 ml. of 0.033 molar stannous octoate in toluene solution. The initial polymerization is carried out at 150° C. and the reactor then further charged with 27.1 grams (0.233 mole) glycolide. The polymerization is continued for approximately 2½ hours at a temperature of from 190° C. to 205° C. A percent conversion of greater than 80% is attained. The resultant copolymer has an inherent viscosity of 1.00 dl/g as measured using a 0.1 g/dl solution in HFIP at 25° C. The resultant copolymer contains 23 percent by weight of ε-caprolactone moieties.

EXAMPLE IX

The procedure as set forth in Example VIII is followed as set forth therein except that 17.12 grams of ε-caprolactone and 10.15 grams of glycolide are used initially, 30.47 grams of glycolide are added prior to the second polymerization and the second polymerization is carried out at 205° C. for 6¼ hours. A percent conversion of approximately 90% is attained. The resultant copolymer has a viscosity of 1.23 dl/g as measured using a 0.1 g/dl solution in HFIP at 25° C. The resultant copolymer contains 22 percent by weight of ε-caprolactone moieties.

EXAMPLE X

A series of experiments is run at various ratios of ε-caprolactone and glycolide as shown in the following Table 1. A flame dried 100 ml glass ampoule equipped with a Teflon-coated magnetic spinbar is charged with ε-caprolactone and glycolide in the amounts shown in the following table and 0.1182 gram 1,6-hexanediol and a catalytic amount of stannous octoate (0.25 ml of a 0.033 molar solution in toluene). The pressure in the ampoule is reduced to evaporate the toluene. After repeated purging and venting with nitrogen the pressure is adjusted with nitrogen to about ¾ of an atmosphere and the ampoule is flame sealed. The reactor is immersed in a silicone oil bath preheated to 100° C. This temperature is maintained for 15 minutes with stirring and then raised to 150° C. This temperature is maintained for 15 minutes and then raised to 190° C. which is maintained for 18 hours. This procedure is followed with examples a through h, however, with example i, the temperature is raised to 205° C. which is maintained for 2 hours. The bath is allowed to cool to 190° C. which is maintained for the final heating period; the cooling period and final heating period total 18 hours. The polymers from each example are isolated, chilled and ground. The percent conversion and inherent viscosity as measured using a 0.1 g/dl solution in HFIP at 25° C. for each copolymer are given in the following Table 1.

TABLE 1

| Experiment | Grams (Moles) ε-caprolactone | Grams (Moles) Glycolide | % Conversion | Inherent Viscosity | Final Wt. ε-caprolactone |
|---|---|---|---|---|---|
| a | 2.84 (0.025) | 54.86 (0.47) | 98 | insoluble | 4 |
| b | 5.70 (0.050) | 52.53 (0.45) | 98 | insoluble | 9 |
| c | 8.56 (0.075) | 49.33 (0.425) | 98 | 1.45 | 14 |
| d | 11.42 (0.100) | 46.43 (0.4) | 97 | 1.48 | 18 |
| e | 14.27 (0.125) | 43.53 (0.375) | 97 | 1.41 | 23 |
| f | 17.12 (0.150) | 40.62 (0.349) | 97 | 1.39 | 28 |
| g | 19.98 (0.175) | 37.72 (0.324) | 97 | 1.39 | 33 |
| h | 17.12 (0.150) | 40.62 (0.349) | 95 | 1.74 | 27 |
| i | 17.12 (0.150) | 40.62 (0.349) | 93 | 1.61 | 25 |

EXAMPLE XI

A flame dried 100 ml. glass ampoule equipped with a Teflon-coated magnetic spinbar is charged with 22.8 grams (0.200 moles) ε-caprolactone, 34.8 grams (0.300 moles) glycolide, 0.1182 grams (0.001 mole) 1,6-hexanediol, and 0.25 ml of a 0.033 mole stannous octoate in toluene solution. The reactor is immersed in a silicone oil bath preheated to 100° C. This temperature is maintained for 15 minutes with stirring. The temperature is increased to 150° C. and maintained for 30 minutes and then increased to 190° C. which is maintained for 17 hours. The polymer is isolated, ground and dried under vacuum at room temperature. Some unreacted monomer is remove by heating the ground polymer at reduced pressure at 110° C. for 16 hours. A conversion of monomer to polymer of better than 90% is obtained. The resultant copolymer has an inherent viscosity of 1.39 dl/g in HFIP at 25° at a concentration of 0.1 g/dl.

In this example, the resultant copolymer contains about 37% by weight of ε-caprolactone moieties and the resulting copolymer is practically amorphous. It is unsuitable for manufacturing dimensionally stable oriented filaments and surgical sutures.

EXAMPLE XII

A flame dried 100 ml ampoule equipped with a Teflon-coated magnetic spinbar is charged with 11.41 g. of ε-caprolactone (0.4 mole), 0.0739 g. 1,b-hexanediol (0.625 m.mole), and a catalytic amount of stannous octoate (0.25 ml. of an 0.033 molar solution in toluene). The pressure in the ampoule is reduced to evaporate the toluene. The ampoule is repeatedly purged and vented with dry nitrogen and the pressure adjusted with dry nitrogen to about ¾ atmosphere. The ampoule is sealed with a flame. The sealed ampoule is immersed in a silicone oil bath preheated to 100° C. This temperature is maintained for 15 minutes, stirring when possible, and the temperature increased to 150° C. and maintained for 15 minutes. The temperature is raised to 190° C. and the polymerization continues for 18 hours at 190° C. The resultant terpolymer is isolated, chilled, ground, and dried under vacuum at room temperature. Some unreacted monomer is removed by heating the ground terpolymer under vacuum at 110° C. for 16 hours; a weight loss of 2.8 percent is experienced. The inherent viscosity of the resultant terpolymer is 1.48 dl/g. in. in 0.1 g/dl solution in hexafluoroisopropanol (HFIP) at 25° C.

The new synthetic absorbable copolymers of the present invention may be converted to oriented filament materials by techniques of extruding and drawing well known in the art for producing filamentous materials. The filaments may be sterilized with or without attached needles to produce sterile surgical sutures as is well-known in the art. A preferred technique for extruding and drawing the copolymers of the present invention is described in the following Example.

EXAMPLE XIII

The copolymer is melt spun in an Instron Rheometer at a temperature at least 10° C. above the melting temperature of the copolymer. A 40 mil die with a L/D ratio of 24 is used. A sheer rate of 213 sec$^{-1}$ is used for the extrusion. The extrudate is taken up through ice water and wound on a spool. The wound fibers are stored at reduced pressure for 2 to 24 hours. The monofilaments are oriented by drawing in one or two stages. The drawn filaments are heat set by heating at the desired temperature under constant strain with or without allowing for 5% relaxation.

The filamentary materials are usually annealed as is well-known in the art under conditions which improve suture properties. The filaments may be annealed under tension at temperatures of from about 50° C. to 120° C. for periods of time of from 1 hour to 48 hours. In preferred embodiments we anneal our filament materials under tension at temperatures of from 60° C. to 110° C. and at times from 4 to 16 hours.

The filament materials are tested for various physical properties such as knot tensile strength, straight tensile strength, elongation, and Young's modulus. The copolymers also may be tested for inherent viscosity, melting temperature and percent crystallinity.

The following describes the various test methods used to determine the properties of the filament materials and/or the copolymers.

The characteristic properties of the filaments of the present invention are readily determined by conventional test procedures. The properties are determined using an Instron tensile tester under the following conditions:

crosshead speed (XH): 2 in/min
Chart speed (S): 10 in/min
Sample length (GL): 2 in
Scale load (SL): 21 lbs/in.

Young's modulus is calculated from the slope of the stress-strain curve of the sample in the initial linear, elastic region as follows:

$$\text{Young's Modulus (psi)} = \frac{\tan\theta \times GL \times CS \times SL}{XH \times XS}$$

$\theta$ is the angle between the slope and the horizontal, XS is the initial cross-sectional area of the fiber (in$^2$), SL is the scale load and XH, CS, and GL are as identified above.

The straight tensile strength is calculated by dividing the force required to break (lbs) by the initial cross-sectional area of the fiber (in$^2$). The elongation to break is read directly from the stress-strain curve of the sample allotting 10% per inch of horizontal displacement.

The knot tensile strength of a filament is determined in separate experiments. The test article is tied into a surgeon's knot with one turn of the filament around flexible tubing (¼ inch inside diameter and 1/16 inch wall thickness). The surgeon's knot is a square knot in which the free end is first passed twice, instead of once, through the loop and pulled taut, then passed once through a second loop, and the ends drawn taut so that a single knot is superimposed upon a compound knot. The first knot is started with the left end over the right end and sufficient tension is exerted to tie the knot securely. The specimen is placed in the Instron tensile tester with the knot approximately midway between the clamps. The knot tensile strength is calculated by dividing the force required to break (lbs) by the initial cross-sectional area of the fiber (in$^2$).

The temperature profile of a copolymer is determined using a Differential Scanning Calorimeter (DSC) by first heating the copolymer to its initial melting temperature ($T_m$ initial) followed by rapid cooling the melted sample. The quenched coplymer is then reheated at a rate of 20° C. per minute and the glass transition temperature ($T_g$), temperature of crystallization ($T_c$) and melting temperature ($T_m$) observed. The crystallinity of the polymer as reported is measured by X-ray diffraction techniques as are well-known.

In all instances the inherent viscosity reported is measured at 25° C. at a concentration of 0.1 g/dl in hexafluorispropyl alcohol (HFIP).

The composition of the final copolymer is determine by NMR analysis.

The various copolymers produced in Examples I through XII are measured for one or more of the following properties: inherent viscosity, melting temperatures and percent crystallinity. The results of these tests are given in the following Table 2:

TABLE 2

| Example | % ε-Caprolactone In Copolymer | Inherent Viscosity dl/g | $T_m$ Initial | % $T_g$ | $T_c$ | $T_m$ | % Crystallinity |
|---|---|---|---|---|---|---|---|
| I | 23 | 1.66 | | 12 | 75 | 165 | 33 |
| II | 15 | Insoluble | 225 | | | 210 | |
| III | 15 | Insoluble | 221 | 22 | 115 | 203 | 26 |
| IV | 26 | 1.53 | 166 | 10 | 86 | 156 | 31 |
| V | 23 | 1.24 | | | | | |
| VI | 17 | 1.62 | 184 | 21 | 78 | 178 | 17 |
| VII | 26 | 1.60 | 185 | 14 | | 188 | 35 |
| VIII | 23 | 1.00 | 222 | | 110 | 213 | 23 |
| IX | 22 | 1.23 | | | | | 33 |
| Xa | 5 | Insoluble | | | | | |
| Xb | 10 | Insoluble | | | | | |
| Xc | 15 | 1.45 | 225 | 20 | 84 | 201 | 40 |
| Xd | 20 | 1.48 | 221 | 18 | 98 | 200 | 34 |
| Xe | 25 | 1.41 | | | | | |
| Xf | 35 | 1.39 | | | | | |
| Xg | 35 | 1.39 | | | | | |
| Xh | 27 | 1.74 | 223 | 26 | 90 | 208 | 26 |
| Xi | 25 | 1.61 | | | | | 21 |
| XI | 37 | 1.39 | | | | | practically |
| XII | — | 1.48 | — | — | — | — | amorphous |

The copolymers of the present inention produced in accordance with the previously described Examples 1 through XII are converted to filament materials where possible as previously described. In some instances the filaments are annealed while in other instances they are not annealed. The resultant filament materials are measured for one or more of the following properties: straight tensile strength, knot tensile strength, elongation, and Young's modulus.

The results of these tests are provided in the following Table 3.

TABLE 3

| Example No. | Drawing Conditions Extrusion Temp °C. | Bath | 1st Stage (Draw Ratio/°C.) | 2nd Stage | Annealing Conditions Relax % | °C./hr | Diam. mils. | Straight Tensile Kpsi | Knot Tensile Kpsi | Elongation % | Young Modulus Kpsi |
|---|---|---|---|---|---|---|---|---|---|---|---|
| I | 240 | Glycerine | 5/52 | 1.2/74 | 5 | 80/6 | 7.8 | 88 | 54 | 30 | 38 |
| II | 240 | Glycerine | — | Not orientable to dimensionally stable fiber | | | | — | — | — | — |
| III | 220 | Glycerine | 4/54 | 1.375/73 | — | non-uniform fiber | | — | — | — | — |
| IV | 180 | Glycerine | 4/52 | 1.51/71 | 0 | 110/5 | 7.8 | 89 | | 43 | 79 |
| V | 185 | Glycerine | 5/51 | 1.2/71 | 0 | 65/6 | 8.0 | 75 | 52 | 28 | 101 |
| VI | 215 | Glycerine | 5/53 | 1.2/75 | 5 | 80/6 | 7.5 | 114 | — | 19 | 689 |
| VII | 225 | Glycerine | 5/52 | 1.2/74 | 0 | 76/16 | 7.2 | 111 | 67 | 42 | 323 |
| VIII | 180 | Glycerine | 4/61 | 1.5/60 | 0 | 65/6 | 8.1 | 59 | 43 | 25 | 94 |
| IX | 185 | Glycerine | 5/49 | 1.2/72 | 5 | 80/6 | 7.5 | 85 | 65 | 25 | 156 |
| Xa | 235 | Glycerine | 5/51 | — | 5 | 80/6 | 6.9 | 90 | — | 35 | 1131 |
| Xb | 230 | Glycerine | 5/52 | 1.2/74 | 5 | 80/6 | 6.9 | 21 | — | 45 | 668 |
| Xc | 235 | Glycerine* | 4/RT* | 1.5/72 | 5 | 80/6 | 7.4 | 36 | — | 42 | 386 |
| Xd | 240 | Glycerine | 5/54 | 1.2/70 | 5 | 80/6 | 7.3 | 56 | 67 | 17 | 301 |
| Xe | 225 | Glycerine | 5/54 | 1.2/75 | 5 | 80/6 | 7.5 | 82 | — | 32 | 100 |
| Xf | 220 | Glycerine | 5/51 | 1.2/73 | 5 | 80/6 | 7.5 | 55 | — | 32 | 88 |
| Xg | 220 | Glycerine | 5/53 | 1.2/74 | 5 | 80/6 | 7.5 | 21 | — | 59 | 38 |
| Xh | 240 | Glycerine | 5/54 | 1.2/74 | 5 | 80/6 | 7.1 | 62 | 50 | 40 | 48 |
| Xi | 180 | Glycerine | 5/56 | 1.2/70 | 5 | 80/6 | 7.1 | 62 | 50 | 40 | 48 |
| XI | Not orientable | | — | — | — | — | — | — | — | — | — |
| XII | 230 | Glycerine | 5/51 | 1.2/74 | — | None | 7.5 | 63 | 51 | 59 | 75 |

*1st stage at room temperature in air; second stage in glycerine.

Fibers made from copolymers produced in accordance with some of the Examples previously described are annealed and sterilized and tested for absorption characteristics. The percent breaking strength retention after various lengths of time is determined.

The breaking strength of a sample is determined by implanting two strands of a sample in the dorsal subcutis of each of eight (8) Long-Evans rats. Thus, 16 strands of each sample are implanted corresponding to the two implantation periods; eight examples of each sample for each of the periods. The periods of in vivo residence are 7 and 14 days. The ratio of the mean value (of 8 determinations) of the breaking strength (determined with an Instron Tensile tester in accordance with standard testing procedure) at each period to the mean value (of 8 determinations) obtained for the sample prior to implantation constitutes its breaking strength for that period.

Table 4 provides the results of the breaking strength retention for the examples as indicated.

TABLE 4

| Example No. | Processing Conditions Annealing | Sterilization | % Breaking Strength Retension At 7 days | 14 days |
|---|---|---|---|---|
| IV | 5 hr./110° C. | Ethylene Oxide | 44 | 11 |
| VII | 16 hr./76° C. | Cobalt 60 | 62 | 37 |
| I | 6 hr./80° C. | Cobalt 60 | 54 | 13 |
| Xh | 6 hr./80° C. | Cobalt 60 | 52 | 12 |
| Xi | 6 hr./80° C. | Cobalt 60 | 49 | 11 |
| Xe | 6 hr./80° C. | Cobalt 60 | 58 | 24 |
| Xf | 6 hr./80° C. | Cobalt 60 | 61 | 22 |

The filaments of the present invention may be used as mono-filament or multifilament sutures and may be woven, braided, or knitted. The polymers of the present invention are also useful in the manufacture of cast films and other solid surgical aids as are well known in the art.

Many different embodiments of this invention will be apparent to those skilled in the art and may be made without departing from the spirit and scope thereof. It is understood that this invention is not limited to the specific embodiments thereof except as defined in the appended claims.

What is claimed is:

1. A process for producing a copolymer of glycolide and ε-caprolactone comprising:

forming a low molecular weight pre-polymer of ε-caprolactone and glycolide, said pre-polymer comprising more than 50 weight percent of ε-caprolactone, and being produced at a temperature of below 220° C., and adding additional glycolide to said pre-polymer and polymerizing said mixture containing the additional glycolide at a temperature above 140° C. for a period of time sufficient to produce a conversion to copolymer of at least 80 percent and copolymer having a crystallinity of at least 5 percent.

2. A process according to claim 1 in which the pre-polymer has at least 60 weight percent ε-caprolactone.

3. A process according to claim 1 wherein the low molecular weight pre-polymer is produced using metal salt or metal oxide.

4. A process according to claim 2 wherein from about 0.004 to 0.02 weight percent of catalyst is used.

5. A process according to claim 4 wherein the catalyst is stannous octoate.

6. A process according to claim 5 wherein a conversion to copolymer of at least 90 percent is obtained.

* * * * *